US005736505A

United States Patent [19]
Manzo et al.

[11] Patent Number: 5,736,505
[45] Date of Patent: Apr. 7, 1998

[54] NON-ALCOHOLIC PERFUME OR COLOGNE

[75] Inventors: Robert P. Manzo, Goshen, N.Y.; Diane M. Kennedy, Bayonne, N.J.

[73] Assignee: Dragoco, Inc., Totowa, N.J.

[21] Appl. No.: 706,119

[22] Filed: Aug. 30, 1996

[51] Int. Cl.$^6$ .................................................... A61K 7/46
[52] U.S. Cl. ........................... 512/2; 512/3; 424/401
[58] Field of Search ............................ 512/2, 3; 424/401

[56]  References Cited

U.S. PATENT DOCUMENTS

| | | | |
|---|---|---|---|
| 5,283,056 | 2/1994 | Chung et al. | 512/3 |
| 5,314,684 | 5/1994 | Horoschak. | |
| 5,374,614 | 12/1994 | Behan et al. | 512/3 |
| 5,389,607 | 2/1995 | Dartnell et al. | 512/3 |
| 5,468,725 | 11/1995 | Guenin. | |
| 5,514,367 | 5/1996 | Lentini. | |
| 5,585,343 | 12/1996 | McGee et al. | 512/3 |
| 5,589,177 | 12/1996 | Herb et al. | 424/401 |
| 5,597,576 | 1/1997 | Genova et al. | 424/401 |
| 5,603,940 | 2/1997 | Candau et al. | 424/401 |
| 5,605,651 | 2/1997 | Balner | 424/401 |

OTHER PUBLICATIONS

Phoenix Chemical, Inc. "Specifications" Dated Jun. 28, 1995.

*Primary Examiner*—James H. Reamer
*Attorney, Agent, or Firm*—Stephan A. Pendorf, P.A.

[57]  ABSTRACT

A non-alcoholic fragrance carrier with good fragrance solubility, product stability and clarity, and silky, non-tacky rub out when applied to the skin. Glycereth-7-triacetate is used for solubilization of fragrance oil into a non-alcohol water system. The ultimate fragrance carrier product is, e.g., a perfume or cologne composition, and contains a reduced overall surfactant level and reduced overall solids level. The composition thus minimizes the use of ingredients which tend to adversely affect evaporation rates, skin feel, rub-out time, and product turbidity.

20 Claims, No Drawings

NON-ALCOHOLIC PERFUME OR COLOGNE

FIELD OF THE INVENTION

The present invention relates to a non-alcoholic fragrance carrier, such as a perfume or cologne, which exhibits acceptable fragrance solubility and a smooth, silky, non-tacky rub out. More specifically, the invention concerns a non-alcoholic, water based perfume or cologne composition which can be formulated with a reduced overall surfactant level and reduced overall solids level. The composition thus minimizes the use of ingredients which tend to adversely affect evaporation rates, skin feel, rub-out time, and product turbidity.

BACKGROUND OF THE INVENTION

Aromatic compositions for wear on the body have been in existence in one form or another throughout the history of mankind. Most natural aromatic compounds are found in the form of oils. For example, East Indian Sandalwood oil is a precious perfumery material known from antiquity. This oil is widely used in perfumery even today.

An early refinement over simply rubbing scarce natural oils onto the body came from mixing natural fragrance oils with other oils to create a solution which was easier to apply and which extended the supply of precious oils. In modern times alcohol, primarily ethyl alcohol, has been added to the oily solution as a diluent for the oils and as carrier, thereby forming modern colognes and perfumes. Alcohols allow for easy dissolution of the perfume oils into a clear, transparent, homogeneous solution. Alcohols are also desirable for their antiseptic properties.

Most importantly, low molecular weight alcohol such as ethanol has the aesthetic property of evaporating quickly, cooling the skin and leaving behind just the fragrance essence. The volatility of lower alcohols is believed to aid in the phase transition of aromatic compounds into the atmosphere. These combined properties give perfumes and colognes an important refreshing feeling when applied to the skin. Alcohol based formulations generally containing from 50 to 90 wt % low molecular weight alcohol remain the current state of perfumes and colognes.

As the world becomes more and more crowded, and as people spend more time in enclosed environments such as office buildings where air is merely filtered and recirculated rather than replaced, governments, especially in the United States, have increased the regulation over the use of volatile organic compounds (VOCs). Alcohol is one of the VOCs which is increasingly being subjected to regulation, with the regulations becoming more and more stringent as the years go by.

Pressure is now being felt by the cologne and perfume industry to reduce the quantity of alcohol in the product. It would be desirable to have a water-based perfume if such a perfume could have the look and feel of an alcohol-based perfume. However, fragrance oils do not dissolve in water, and it is a challenge to achieve an alcohol-free formulation acceptable to the consumer accustomed to the physical properties of alcohol based perfume compositions, primarily the clarity and transparency, the clean feeling on the skin, the rapid evaporation rates, and the non-staining properties on skin and clothing.

Perfumes are formulations wherein hundreds of discrete organic, hydrophobic fragrance ingredients are blended to produce a final scent. Any attempt to replace part or all of the alcohol in perfume or cologne formulations with non VOCs changes the solubility and physico-chemical environment of the aromatic compounds and requires a reformulation of the diluent and emulsifier in an attempt to achieve final scent and tactile properties similar to alcohol containing perfumes or colognes. Reduced solubility can even result in the fragrance compounds precipitating out the solution. Enhancing solubilization by utilization of common surfactants and emulsifiers results in a tacky, soapy, impure feeling on the skin. That is, surfactants are surface active agents, compounds which generally have a hydrophobic and a hydrophilic component, and are added only for their functionality in bridging the gap between the hydrophobic and hydrophilic phases and improving solubility. While surfactants are necessary to facilitate disolution or dispersion of fragrance oils in water, they otherwise detract from the final composition, and it is preferred to utilize as little surfactant as possisble.

One approach to providing a perfume low in VOCs has been to provide a fragrance delivering compositions as a dry powder. However, while this approach solves the problem of VOCs, the physical properties of the product is so different from traditional perfume compositions as not to be considered as providing an acceptable substitute for perfumes.

U.S. Pat. No. 5,468,725 (Guenin, et al.) teaches an alcohol-free transparent perfume containing an alcohol-free perfume base, water and a stable transparent oil-in-water microemulsion concentrate formed of water, at least one hydrophobic perfume oil, at least one cationic surfactant and at least one non-ionic surfactant in the absence of lower alkanols, with a specified mixing ratio of water, oil and from 6 to 12 wt % surfactant. In particular, a non-ionic surfactant and a small amount of cationic surfactant is used with an aqueous system of a fragrance oil to enhance the transparency of the alcohol-free fragrance microemulsion. However, cationic surfactants are "essential" to the formation, as discussed in column 5, first paragraph. These positively charged surfactants may effect the chemical stability of the perfume base. Further, the increased reliance on surfactant increases solids content and detracts from clean rub out on the skin.

The consumer demands a perfume or cologne which, when applied to the skin, imparts a feeling of freshness and cleanliness. This is not achieved by increasing surfactants but by decreasing surfactants. Accordingly, there is a need for a non-alcohol perfume or cologne with a lower overall surfactant level, less of a tacky feel on the skin, low turbidity and a superior clean, pure, silky, nontacky feel upon application to the skin.

SUMMARY OF THE INVENTION

Following extensive experimentation, the present inventors discovered that a unique non-alcoholic fragrance carrier could be provided which exhibits good fragrance solubility and product stability and clarity, and yet gives a pleasant smooth, silky, non-tacky rub out when applied to the skin. The key to the formulation is the use of glycereth-7-triacetate as solubilization aid. This unique ester allows solubilization of fragrance oil into a non-alcohol water system while maintaining a smooth, non-tacky rub out. The non-alcohol water system preferably includes non-ionic surfactants and, more preferably, contains no cationic surfactants. The fragrance carrier may be a perfume base or a perfume or cologne end product formulation, and contains a reduced overall surfactant level and reduced overall solids level. The composition thus minimizes the use of ingredients which tend to adversely affect evaporation rates, skin feel, rub-out time, and product turbidity. The end product is a non-alcohol perfume or cologne with a lower overall surfactant level, less of a tacky feel on the skin, low turbidity and a superior clean, pure, silky, nontacky feel upon application to the skin.

The foregoing has outlined rather broadly the more pertinent and important features of the present invention in order that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or formulating other fragrance carriers for carrying out the same purposes of the present invention. It should also be realized by those skilled in the art that such equivalent formulations do not depart from the spirit and scope of the invention as set forth in the appended claims.

DETAILED DESCRIPTION OF THE INVENTION

For brevity, the term "perfume composition" will be used in this specification when referring to consumer ready, final product compositions according to the invention. It will be understood, however, that the invention is not limited to only traditional perfumes, but includes after-shave, cologne, insect repellents, sun-burn or insect bite medications, and other water based non-alcoholic transparent fragrance or pharmaceutical compositions wherein a hydrophobic active ingredient is to be solubilized in a non-alcoholic carrier such as water, and wherein the product is clear, transparent, and has good rub our qualities on the skin. The invention also includes non-alcoholic perfume bases used in formulating non-alcohol perfumes.

Perfume bases in the context of this invention are any of the concentrated hydrophobic aromatic compositions which contain the mixture of primary aromatic ingredients which are then dissolved or dispersed in one or more of carriers (which in the present invention is water), vehicles (e.g., a non-toxic glycol such as propylene glycol), solvents, dispersents, emulsifiers, surface-active agents, aerosol propellants and the like to form a final perfume or fragrance carrier composition. Any of these ingredients may be used in the present invention so long as they are selected from those which do not impart an oily or tacky feel to the final perfume composition. These additional ingredients provide the environment for the aromatic ingredients and influence the final scent, feel, and stability of the perfume composition. Ingredients which positively contribute to stability, clarity, scent, and feel of the composition are preferred.

Accordingly, the non-alcoholic transparent perfume composition of the present invention comprises as main ingredients:

(i) from 0.05 to 50 wt. % of hydrophobic fragrance compound(s), preferably 2 to 20 wt. %, (ii) from 0.01 to 15 wt. % glycereth-7-triacetate, preferably 3–12 wt %, (iii) a non-ionic surfactant, preferably less than 6 wt %, and (iv) water, preferably from 50 to 80 wt %.

The amount of glycereth-7-triacetate is most preferably merely that minimum amount which works in conjunction with non-ionic surfactant to reduce the overall amount of surfactant and to sufficiently dissolve the hydrophobic fragrance composition in the predetermined amount of water to produce a clear, transparent composition with good, non-tacky skin feel. Accordingly, the amount of glycereth-7-triacetate depends not only on the type and amount of hydrophobic fragrance compound(s), but also on any other carriers, vehicles, solvents, dispersents, emulsifiers, surface-active agents, and aerosol propellants which may be present.

The glycereth-7-triacetate is preferably mixed into the hydrophobic fragrance compound prior to addition of the hydrophobic fragrance compound into water.

Hydrophobic fragrance compounds

The hydrophobic fragrance bases are usually compounded as blends of tens or hundreds of individual aromatic hydrophobic ingredient compounds. Any of the fragrance compounds or bases conventionally employed in the art may be used in the present invention, and include, for example, natural perfume oils (sandalwood oil, lavender oil, etc.), synthetic perfume oils, aromatic alcohols, aromatic aldehydes, aromatic ketones, aromatic esters, aromatic lactones, aromatic nitriles and other aromatic hydrocarbons. These fragrance oils or components are generally supplied as blends in the form of perfume bases so that the combined odors of the individual components produce a pleasant or desired fragrance.

Such perfume bases usually contain (a) the main note or the "bouquet" or foundation-stone of the composition; (b) modifiers which round-off and accompany the main note; (c) fixatives which include odorous substances which lend a particular note to the perfume throughout all stages of evaporation, and substances which retard evaporation; and (d) top-notes which are usually low-boiling fresh-smelling materials.

The fragrance composition of the present invention includes concentrated perfume bases which are subsequently formulated into more dilute perfume compositions, as well as the perfumes ready to be sold to the consumer prepared from these concentrated perfume bases. The key to the formulations of the present invention is the presence of the above-listed essential ingredients, and particularly glycereth-7-triacetate.

Water phase

The water phase can be pure water or may contain small amounts (e.g., less than 1%) of preservative, UV-absorber, antimicrobial agent, humectant, or other additive conventionally employed in the art. For example, a coloring agent, preferably a water-soluble coloring agent, may be added to the water phase, and examples of colorants include Food, Drug and Cosmetic Agency approved colors.

Glycereth-7-Triacetate

The key to the formulation according to the present invention is glycereth-7-triacetate (sold under tradenames such as PELEMOL G7A by Phoenix Chemical and DERMOL GL-7A by Alzo). This unique ester allows solubilization of fragrance oil into a water system while maintaining a smooth, non-tacky rub out. Glycereth-7-triacetate participates in the solubilization of fragrance oil into the formula in a way which makes it possible to minimize the requirement for those non-fragrance ingredients which can affect evaporation rates, skin feel and rub-out time.

Glycereth-7-triacetate is available from Phoenix Chemical, New Jersey as a humectant/emollient under tradename PELEMOL G7A as a non-irritating and non-toxic clear oily liquid, with a color on the Gardner scale of 2 or less, a mild odor, a saponification value of 305–330, an acid value of 7 maximum, and a hydroxyl value of 20.0 maximum.

This effect is surprising in that other esters such as isopropyl myristate, isopropyl palmitate and similar products all require an emulsifier to form a homogenous solution. This increased reliance on surfactant increases solids content and tacky feeling.

It is further surprising to note that the amount of surfactant can be substantially reduced in accordance with the present invention. For example, the amount of surfactant in a conventional non-alcohol perfume formulation currently on the market (comprising water, propylene glycol, isoceteth 20, fragrance, nonoxynol 13, PEG-30 glyceryl isostearate, PPG-5-ceteth-20, methylparaben, propylparaben, butylparaben, chlorphenesin, phenoxyethanol, and FD&C Red #40) is in the range of 6 to 12 wt % measured as solids. In accordance with the present invention the amount of surfactant can be reduced to about 2 to 6 wt % measured as solids.

Non-ionic surfactant

The formulation according to the invention preferably contains non-ionic surfactants. The non-ionic surfactants used for in the practice of invention can be selected from those well known in the art as non-ionic surfactants employed in perfumes. Most preferred are surfactants having a hydrophilic/lipophilic balance (HLB) value of 11–17.

Examples of suitable surfactants include the following:

TWEEN® 20 (polyoxyethylene (20) Sorbitan Monolaurate);

TWEEN® (is a Trademark of ICI Americans of Wilmington, Del.);

TWEEN® 40 (Polyoxyethylene (20) Sorbitan Monopalmitate);

CREMOPHOR® RH 40 (Ethoxy Hydrogenated Castor Oil) (CREMOPHOR® is a Trademark of BASF Aktiengesellschaft of D-6700 Ludwigshafen, Federal Republic of Germany);

CREMOPHOR® RE 60 (Ethoxy Hydrogenated Castor Oil);

GENAPOL® (Alcohol Polyglycol Ether) (GENAPOL® is a trademark of Hoechst Aktiengesellschaft of D-6230 Frankfurt AM Main No. 90, Postfach 80, Federal Republic of Germany);

TRYCOL brand surfactants available from Henkel Corp./Emery Group, Ohio.

TERGITOL surfactants made by Union Carbide Corp., Conn.

Nonionic surfactants are typically compounds produced by the condensation of alkylene oxide groups (hydrophilic in nature) with an organic hydrophobic compound, which can be aliphatic or alkyl-aromatic in nature, but can include other surfactants that do not possess a charge group. The length of the hydrophilic or polyoxyalkylene radical which is condensed with any particular hydrophobic group can be readily adjusted to yield a water-soluble compound having the desired degree of balance between hydrophilic and hydrophobic elements.

For example, surfactants can be formed by condensing ethylene oxide with a hydrophobic base formed by the condensation of propylene oxide with propylene glycol. The hydrophobic portion of the molecule which, of course, exhibits water insolubility has a molecular weight of from about 1,500 to about 1,800. The addition of polyoxyethylene radicals to this hydrophobic portion tends to increase the water solubility of the molecule as a whole and the liquid character of the products is retained up to the point where polyoxyethylene content is about 50% of the total weight of the condensation product.

Examples of classes of nonionic surfactants are:

Alkyl phenol ethoxylates. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds can be derived from polymerized propylene, diisobutylene, octane, or nonane, for example.

Polyethylene glycol/polypropylene glycol block copolymers. Those derived from the condensation of ethylene oxide with the product resulting from the reaction of propylene oxide and ethylene diamine products which can be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

Fatty alcohol and fatty acid ethoxylates. The condensation product of aliphatic alcohols having from 8 to 18 carbon atoms, in either straight chain or branched chain configuration with ethylene oxide, e.g., a coconut alcohol ethylene oxide condensate having from 10 to 30 moles of ethylene oxide per mole of coconut alcohol, the coconut alcohol fraction having from 10 to 14 carbon atoms. Other ethylene oxide condensation products are ethoxylated fatty acid esters of polyhydric alcohols (e.g., Tween 20-polyoxyethylene (20) sorbitan monolaurate).

Long chain tertiary amine oxides. Long chain tertiary amine oxides corresponding to the following general formula:

$$R_1R_2R_3N \rightarrow O$$

wherein $R_1$ contains an alkyl, alkenyl or monohydroxy alkyl radical of from about 8 to about 18 carbon atoms, from about 0 to about 10 ethylene oxide moieties, and from 0 to 1 glycerol moiety, and $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyldi(2-hydroxy ethyl) amine oxide, dimethyloctylamine oxide, dimethyldecyiamine oxide, dimethyltetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl) amine oxide, dimethylhexadecylamine oxide.

Alkyl polysaccharide (APS) surfactants such as the alkyl polglycosides. Such surfactants are APS surfactants having a hydrophobic group with about 6 to about 30 carbon atoms and polysaccharide (e.g., polyglycoside) as the hydrophilic group. Optionally, there can be a polyalkylene-oxide group joining the hydrophobic and hydrophilic moieties. The alkyl group (i.e., the hydrophobic moiety) can be saturated or unsaturated, branched or unbranched, and unsubstituted or substituted (e.g., with hydroxy or cyclic rings).

Polyethylene glycol (PEG) glycerol fatty esters, such as those of the formula $R(O)OCH_2CH(OH)CH_2(OCH_2CH_2)$ $_n$OH wherein n is from about 5 to about 200, preferably from about 20 to about 100, and R is an aliphatic hydrocarbyl having from about 8 to about 20 carbon atoms.

The foregoing non-ionic surfactants can be used taken alone or taken in combination of two or more.

The following table shows how representative main ingredients may be compounded into a formulation according to the present invention:

| Trade Name | Chemical Name | Weight % | Preferred |
|---|---|---|---|
| PART I |  |  |  |
| Fragrance |  | 1–50 | 2–20 |
| Cremophor RH-60 | PEG-60 Hydrogenated Castor Oil | .25–10 | 1–3 |
| Arlasolve 200L | Isoceteth-20 | 0.1–5.0 | 1–3 |
| Tergitol NP-13 | Nonoxynol 13 | 0.1–5.0 | .5–1.0 |
| PELEMOL G7A | Glycereth-7 triacetate | 0.1–15 | 3–12 |
| PART II |  |  |  |
| Propylene Glycol |  | 0.1–50.0 | 5–20 |
| Germaben II | Propylene Glycol and Diazolidinyl Urea, Methylparaben, Propylparaben | 0.1–5.0 | .8–1.5 |
| PART III |  |  |  |
| Deionized Water |  | QS | QS |

In formulating the fragrance carrier according to the present invention, the compositions of Parts I, II, and III are prepared separately, then mixed to give a final composition wherein the amount of individual ingredients is as indicated in the weight percent column.

Specific formulations may be prepared in accordance with the following examples.

COMPARATIVE EXAMPLE 1

The following ingredients were blended at room temperature in accordance with the above protocol.

| Trade Name | Chemical Name | Supplier | Weight % |
|---|---|---|---|
| PART 1 |  |  |  |
| Fragrance oil |  | Dragoco | 2.0 |
| Arlasolve 200L | Isoceteth-20 | ICI | 2.0 |
| Tergitol NP-13 | Nonoxynol 13 | Union Carbide | 1.0 |
| Tagat I | PEG-30 glyceryl isostearate | Goldschmidt | 2.0 |
| Procetyl AWS | PPG-5-Ceteth-20 | Croda | 1.0 |
| PART 2 |  |  |  |
| Propylene Glycol |  |  | 5.0 |
| Germaben II |  | Sutton | 1.1 |
| PART 3 |  |  |  |
| Deionized Water |  |  | 85.9 |
| TOTAL |  |  | 100.0% |

While the perfume composition was clear, the fragrance was not long lasting due to the small quantity thereof. The skin feel after rub out was not satisfactory and required improvement.

COMPARATIVE EXAMPLE 2

The following ingredients were blended in a conventional manner in the indicated amounts.

| Trade Name | Chemical Name | Supplier | Weight % |
|---|---|---|---|
| PART 1 |  |  |  |
| Fragrance oil |  | Dragoco | 5.0 |
| Arlasolve 200L | Isoceteth-20 | ICI | 2.0 |
| Tergitol NP-13 | Nonoxynol 13 | Union Carbide | 1.0 |
| Tagat I | PEG-30 glyceryl isostearate | Goldschmidt | 2.0 |
| Procetyl AWS | PPG-5-Ceteth-20 | Croda | 1.0 |
| PART 2 |  |  |  |
| Propylene Glycol |  |  | 5.0 |
| Germaben II |  | Sutton | 1.1 |
| PART 3 |  |  |  |
| Deionized Water |  |  | 82.9 |
| TOTAL |  |  | 100.0% |

As a result of the increased amount of fragrance oil in Comparative Example 2, the product became hazy. Comparative Example 2 formulated so as to simulate the composition of currently market non-alcohol cologne product.

EXAMPLE 1

The following ingredients were blended in a conventional manner in the indicated amounts.

| Trade Name | Chemical Name | Supplier | Weight % |
|---|---|---|---|
| PART 1 |  |  |  |
| Fragrance oil |  | Dragoco | 5.0 |
| Pelemol G-7A | Glycereth-7-triacetate | Phoenix | 3.0 |
| Cremophor RH-60 | PEG-60 hydrogenated castor oil | BASF | 3.0 |
| Arlasolve 200L | Isoceteth-20 | ICI | 2.0 |
| Tergitol NP-13 | Nonoxynol 13 | Union Carbide | 1.0 |
| Tagat I | PEG-30 glyceryl isostaerate | Goldschmidt | 1.0 |
| Glucam P-10 | PPG-10 methyl glucose ether | Amerchol | 1.0 |
| PART 2 |  |  |  |
| Propylene Glycol |  |  | 10.0 |
| Germaben II | paraben mixture | Sutton | 1.10 |
| PART 3 |  |  |  |
| Deionized Water |  |  | 72.90 |
| TOTAL |  |  | 100.0% |

The product was clear and had good fragrance and stability. However, the high surfactant level contributed to a tacky feeling.

EXAMPLE 2

The following ingredients were blended in a conventional manner in the indicated amounts.

| Trade Name | Chemical Name | Supplier | Weight % |
|---|---|---|---|
| PART 1 |  |  |  |
| Fragrance oil |  | Dragoco | 5.0 |
| Pelemol G-7A | Glycereth-7-triacetate | Phoenix | 5.0 |
| Cremophor RH-60 | PEG-60 hydrogenated castor oil | BASF | 3.0 |
| Arlasolve 200L | Isoceteth-20 | ICI | 2.0 |

-continued

| Trade Name | Chemical Name | Supplier | Weight % |
|---|---|---|---|
| Tergitol NP-13 PART 2 | Nonoxynol 13 | Union Carbide | 1.0 |
| Propylene Glycol | | | 10.0 |
| Germaben II PART 3 | paraben mixture | Sutton | 1.10 |
| Deionized Water | | | 72.9 |
| TOTAL | | | 100.0% |

The product was initially as clear as distilled water. When applied to the skin and rubbed out it did not have a tacky feel. However, after five days of stability testing the product began to turn hazy at ambient and elevated temperatures.

EXAMPLE 3

The following ingredients were blended in a conventional manner in the indicated amounts.

| Trade Name | Chemical Name | Supplier | Weight % |
|---|---|---|---|
| PART 1 | | | |
| Fragrance oil | | Dragoco | 5.0 |
| Pelemol G-7A | Glycereth-7-triacetate | Phoenix | 5.50 |
| Cremophor RH-60 | PEG-60 hydrogenated castor oil | BASF | 3.25 |
| Arlasolve 200L | Isoceteth-20 | ICI | 2.0 |
| Tergitol NP-13 PART 2 | Nonoxynol 13 | Union Carbide | 1.0 |
| Propylene Glycol | | | 12.25 |
| Germaben II PART 3 | | Sutton | 1.10 |
| Deionized Water | | | 69.90 |
| TOTAL | | | |

This product was initially as clear as water, and when rubbed into the skin had a silky, non-tacky feel. In comparison to the perfume composition of Example 1, the composition of Example 3 had a higher glycereth-7-triacetate concentration and as a result had a higher fragrance solubility while at the same time having a 20 wt % reduction in solids content.

Although the non-alcohol perfume composition was described herein with great detail with respect to a water base perfume, it will be readily apparent that the formulation is capable of use in a number of other applications, such as water based pharmaceutical compositions wherein hydrophobic active agents such as insect repellants, antihistamine, etc. are incorporated in water. Although this invention has been described in its preferred form with a certain of particularity with respect to a non-alcohol perfume base, it is understood that the present disclosure of the preferred form has been made only by way of example and that numerous changes in the details of structures and the composition of the combination may be resorted to without departing from the spirit and scope of the invention.

Now that the invention has been described,

What is claimed is:

1. A non-alcoholic transparent fragrant composition comprising:
    (a) a hydrophobic perfume base,
    (b) water,
    (c) a non-ionic surfactant, and
    (d) glycereth-7-triacetate.

2. A perfume composition as in claim 1, wherein said water is present in an amount of from 40 to 95% by weight.

3. A perfume composition as in claim 1, wherein said hydrophobic perfume base is present in an amount of from 0.05% to 50% by weight.

4. A perfume composition as in claim 1, wherein said hydrophobic perfume base is present in an amount of from 1% to 20% by weight.

5. A perfume composition as in claim 1, wherein said hydrophobic perfume base is present in an amount of from 2% to 10% by weight.

6. A perfume composition as in claim 1, wherein glycereth-7-triacetate is present in an amount of from 0.1 to 15% by weight.

7. A perfume composition as in claim 1, wherein said glycereth-7-triacetate is present in an amount of from 3 to 12% by weight.

8. A perfume composition as in claim 1, wherein said glycereth-7-triacetate and non-ionic surfactant are present in an amount effective to solubilize said hydrophobic fragrance in said water.

9. A perfume composition as in claim 1, wherein the amount of glycereth-7-triacetate is from 0.5 to 2.0 times by weight the amount of hydrophobic perfume base.

10. A perfume composition as in claim 1, wherein the amount of glycereth-7-triacetate is from 0.5 to 2.0 times by weight the amount of non-ionic surfactant.

11. A perfume composition as in claim 1, wherein the total amount of surfactant is in the range of from 2 to 6 wt % measured as solids.

12. A perfume composition as in claim 1, wherein said surfactant is a surfactant having a hydrophilic/lipophilic balance (HLB) value of 11–17.

13. A perfume composition as in claim 1, wherein the amount of non-ionic surfactant is in the range of from 2 to 6 wt % measured as solids.

14. A perfume composition as in claim 1, wherein said perfume composition is selected from the group consisting of cologne, perfume, after-shave, insect repellant, sun-burn medication and insect bite medication.

15. A non-alcoholic, cationic surfactant free, non-tacky transparent perfume composition comprising:
    (a) a fragrance oil,
    (b) water,
    (c) non-ionic surfactant, and
    (d) a sufficient amount of glycereth-7-triacetate to solubilize said fragrance oil in said water.

16. A perfume base comprising hydrophobic fragrance oil(s), non-ionic surfactant and glycereth-7-triacetate.

17. A transparent, non-tacky, cationic surfactant free, non-alcoholic, water based pharmaceutical composition comprising:
    (a) one or more hydrophobic topical pharmaceutically active compounds,
    (b) water,
    (c) a non-ionic surfactant, and
    (d) glycereth-7-triacetate.

18. A pharmaceutical composition as in claim 17, wherein said water is present in an amount of from 40 to 95% by weight.

19. A pharmaceutical composition as in claim 17, wherein said hydrophobic pharmaceutically active compounds are present in an amount of from 0.05% to 50% by weight.

20. A pharmaceutical composition as in claim 17, wherein glycereth-7-triacetate is present in an amount of from 0.1 to 15% by weight.

* * * * *